United States Patent
Shimamoto et al.

(10) Patent No.: US 6,486,296 B1
(45) Date of Patent: Nov. 26, 2002

(54) LACTIDE-CONTAINING POLYMER AND MEDICAL MATERIAL

(75) Inventors: Takeshi Shimamoto, Ayabe (JP); Hideji Kagawa, Ayabe (JP)

(73) Assignee: Gunze Limited, Kyoto (JP)

( * ) Notice: Subject to any disclaimer, the term of this patent is extended or adjusted under 35 U.S.C. 154(b) by 0 days.

(21) Appl. No.: 09/701,221

(22) PCT Filed: May 25, 1999

(86) PCT No.: PCT/JP99/02733
§ 371 (c)(1),
(2), (4) Date: Nov. 27, 2000

(87) PCT Pub. No.: WO99/61082
PCT Pub. Date: Feb. 12, 1999

(30) Foreign Application Priority Data

May 28, 1998 (JP) .............................. 10-147841

(51) Int. Cl.[7] .............................. C08G 63/58

(52) U.S. Cl. .................. 528/354; 528/355; 528/491; 528/501; 528/502 C

(58) Field of Search ................ 528/354, 355, 528/501, 502 C, 491

(56) References Cited

U.S. PATENT DOCUMENTS 4,719,246 A * 1/1988 Murdoch et al. ............ 521/134

FOREIGN PATENT DOCUMENTS

| JP | 889567 | 4/1996 |
| WO | 9015629 | 12/1990 |

* cited by examiner

*Primary Examiner*—Duc Truong
(74) *Attorney, Agent, or Firm*—Baker Botts L.L.P.

(57) ABSTRACT

A medical material which contains a lactide-containing polymer having weight-average molecular weight lower than 400000 as determined by GPC and has a lactide content of 4000 ppm or lower.

16 Claims, 3 Drawing Sheets

LACTIDE-CONTAINING POLYMER AND MEDICAL MATERIAL

CROSS-REFERENCE TO RELATED APPLICATIONS

This application is a national phase application of International Application No. PCT/JP99/02733, which was filed on May 25, 1999 and which published in Japanese on Dec. 2, 1999, which in turn claims priority from Japanese Application No. 10/147841, which was filed on May 28, 1998.

TECHNICAL FIELD

The present invention relates to a medical material and a process for producing the same.

BACKGROUND ART

A medical material comprising polylactide which is used in operation has the advantage that it does not need to be taken out of the body after an operation since it is hydrolyzed and absorbed in vivo, while such medical material has a drawback that it is low in retention of strength and deteriorated in strength in vivo in a relatively short period of time. Molecular weight of polylactide has heretofore been increased to improve the strength thereof; however, polylactide tends to be deteriorated in thermal processability if the molecular weight is too high. For example, when polylactide is heated to exceed its melting point for molding, it is largely decreased in the molecular weight due to thermal decomposition. Thus, there is a limit for retaining the strength against heat with maintaining the same molecular weight.

An object of the present invention is to provide a medical material which is excellent in thermal processability and useful as a fixation device or like materials which are required to maintain high strength for a long period of time and a process for producing the same.

DISCLOSURE OF THE INVENTION

Figure 1:
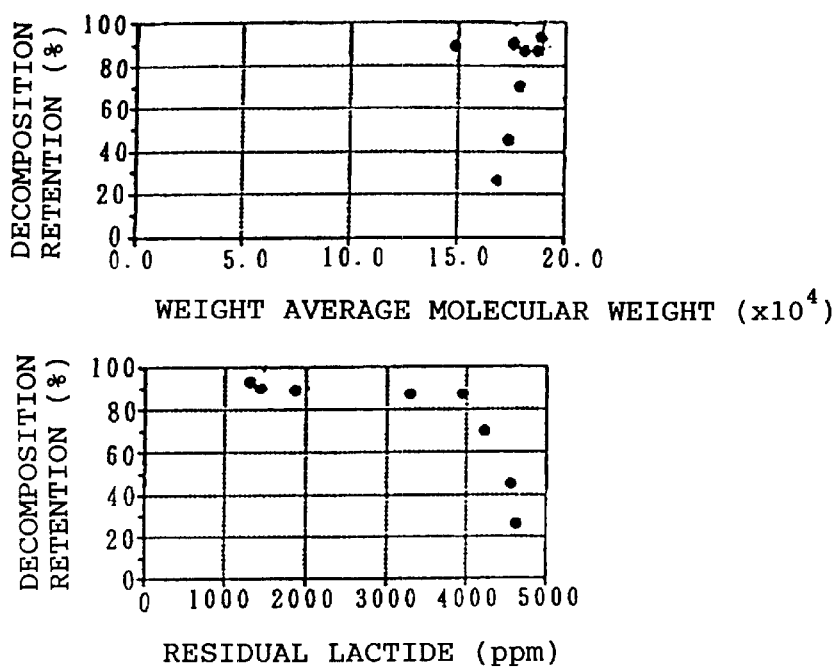
FIG. 1 shows relationships among molecular weight, residual amount of lactide and retention of pull-out strength of each of the PLLA samples obtained in Preparation Examples 1–8.

The inventors conducted an extensive research considering the above drawbacks and found that polylactide having low molecular weight and high retention of strength can be obtained by lowering a content of low molecular lactic acid components, especially of lactide, to be contained therein.

The present invention provides the following medical materials and process for producing the same.

Item 1. A medical material comprising a lactide-containing polymer having weight-average molecular weight measured by GPC of less than 400,000 and has a lactide content of not more than 4,000 ppm.

Item 2. The medical material according to Item 1, wherein initial flexural strength is not less than 100 MPa and flexural strength after being immersed in a phosphate buffered saline (PBS) at 37° C. for 90 days is not less than 80% of the initial strength.

Item 3. The medical material according to Item 1, wherein the medical material is a bone fixation device.

Item 4. The medical material according to Item 3, wherein the bone fixation device is a pin, a screw, a nail, an intramedullary nail, a plate, a washer, a staple, an anchor or a wire.

Item 5. A process for producing a medical material, characterized by reducing a lactide content to be not more than 4,000 ppm by treating a lactide-containing polymer by at least one step selected from the group consisting of (1) a step of vacuum thermodrying, (2) a step of washing with a solvent and (3) a step of reducing a pressure during polymerization.

Item 6. A method for adjusting retention of strength of a medical material, characterized by adjusting a lactide content.

A medical material of the present invention is usable as a bone fixation device (pin, screw, nail, intramedullary nail, plate, washer, staple, anchor, wire), bone spacer, bone prosthesis, suture for operation, a ligature (string), a material for ligament and the like in various forms including a monofilament, thread, knitted fabric, non-woven fabric, woven fabric, various molded articles and so on.

Examples of the lactide-containing polymer include poly-L-lactide (PLLA), poly-D-lactide (PDLA), poly-D,L-lactide (PDLLA), L- D- and DL-lactide-glycolide copolymer (P(LA/GA)) and L- D- and DL-lactide/caprolactone copolymer (P(LA/CL)).

A content of lactide (D, L or DL) in the backbone of the lactide-containing polymer is not less than 30 mol %, preferably not less than 50 mol %, more preferably not less than 70 mol %, yet more preferably not less than 80 molt, particularly preferably not less than 90 mol %. A preferred lactide-containing polymer is PLLA.

Weight-average molecular weight of the lactide-containing polymer measured by GPC is less than 400,000, preferably 50,000–350,000, more preferably 100,000–250,000, particularly preferably 130,000–210,000.

Initial flexural strength of the medical material of the present invention is about 100–300 MPa, preferably about 180–250 MPa.

Retention of flexural strength of the medical material of the present invention after being immersed in phosphate buffered saline (PBS) at 37° C. for 90 days is not less than 80%, preferably not less than 85%, more preferably not less than 90%.

The low molecular weight lactic acid components encompass, in addition to lactide which is a starting material for polymerization, lactic acid, lactic acid dimer, lactic acid trimer and so forth which are formed by thermal decomposition in the course of melt molding.

A content of such lactide is not more than 4,000 ppm, preferably not more than 3,500 ppm, more preferably not more than 3,000 ppm, yet more preferably not more than 2,000 ppm, particularly preferably not more than 1,000 ppm.

Lactide can be reduced to be lower than a predetermined concentration by at least one step selected from the group consisting of (1) a step of vacuum thermodrying, (2) a step of washing with a solvent and (3) a step of reducing a pressure during polymerization.

The step of vacuum thermodrying can be carried out at a pressure of about 1–10 mmHg, for about 10–20 hours and at a temperature of about 120° C.

The step of washing with a solvent can be carried out by immersing a lactide-containing polymer in an organic solvent such as acetone, ethyl acetate, butanol or the like, subjecting the lactide-containing polymer to Soxhlet extraction for 5–12 hours, and then volatizing the organic solvent.

The step of reducing a pressure during polymerization can be carried out by reducing a pressure by several tens of mmHg for several hours when the polymerization has proceeded to a certain stage.

A bone fixation device, which is one of the examples of the medical material of the present invention, is obtainable by melt-molding or extruding a lactide-containing polymer having a lactide content of not more than 4,000 ppm, drawing the molded article and pressing or cutting the drawn article.

According to the present invention, even if the lactide-containing polymer used as a starting material for producing a medical material contains more than 4,000 ppm of lactide, a lactide content of the resulting medical material can be reduced to not more than 4,000 ppm by carrying out a step of vacuum thermodrying or a step of washing with a solvent (i) when the polymer is in the form of polymer chips, (ii) after the melt molding or extrusion, (iii) after the drawing or (iv) after processing as a product by pressing or cutting.

The drawing step can be carried out by an arbitrary method such as a uniaxial, biaxial or multiaxial tension-drawing, solid phase extrusion, hydrostatic extrusion or the like. A draw ratio may typically be about not more than 10. The lactide-containing polymer to be used for the medical material of the present invention may optionally be undrawn.

The medical material of the present invention is obtainable by, for example, pelletizing a lactide-containing polymer having a lactide content of not more than 4,000 ppm using a pelletizer; extruding the pellets by injection molding to obtain a molded article; drawing the molded article by hydrostatic extrusion at a temperature not lower than the glass transition temperature and not higher than the melting point; and cutting using a lathe, fraise and the like or pressing using a molding press.

Examples of materials to be added to the medical material of the present invention include bio-ceramics such as hydroxyapatite, A-W crystallized glass, alumina, zirconia, tricalcium phosphate (TCP), carbon, bio-glass, calcium phosphate and bone growth factors such as BMP (bone morphogenetic protein), TGF-$\beta$, IGF-I and IGF-II (insulin-like growth factors I and II). The bio-ceramics each has a particle size of about 1–300 $\mu$m, and the medical material may comprise such bio-ceramics in an amount of about 1–90%. These materials may be added to the medical material as being kneaded therewith or as being applied as a coating on the surface of the medical material.

As to a process for producing the medical material, it is possible to optimize the retention of flexural strength for each of the use applications by adjusting the amount of lactide to be comprised in the medical material.

A medical material having a lactide content of 100–4,000 ppm is suitably used for parts which are cured within 8–16 weeks such as bones (bone fixation device, bone spacer, bone prosthesis).

A medical material having a lactide content of 1–100 ppm is suitably used as a bone fixation device, bone spacer or bone prosthesis which are required to retain strength for over 16 weeks after an operation (ex. leg extension operation).

A medical material having a lactide content of 5,000–8,000 ppm can be used for parts which are cured within 1–2 weeks such as the muscle and skin.

A medical material having a lactide content of 4,000–5,000 ppm can be used for parts which are cured within 2–8 weeks such as the lung and liver.

The medical material of the present invention can be remarkably improved in retention of various kinds of strength such as pull-out strength, tensile strength and so on in addition to flexural strength even if the medical material is a low molecular polymer.

BEST MODE FOR CARRYING OUT THE INVENTION

The present invention is illustrated based on, but is not limited to, the following examples.

Lactide contents are measured by HPLC under the following conditions.

Detector: RID-6A (product of Shimadzu Corporation);
Pump: LC-9A (product of Shimadzu Corporation);
Column Oven: CTO-6A (product of Shimadzu Corporation);
Column: Serially-arranged Shim-pack GPC-801C, -804C, 806C, -8025C (products of Shimadzu Corporation);
Analysis Conditions:
Solvent: Chloroform;
Flow Rate: 1 ml/min;
Amount of Sample: 200 $\mu$l (0.5 W/W % of a sample was dissolved in chloroform);
Column Temperature: 40° C.

The weight-average molecular weights are measured by GPC under the following conditions.

Detector: RID-6A (product of Shimadzu Corporation);
Pump: LC-6A (product of Shimadzu Corporation);
Column Oven: CTO-6A (product of Shimadzu Corporation);
Column: Serially-arranged shodex K-802, K-804 and K-806 (products of Showa Denko K. K.);
Analysis Conditions:
Solvent: Chloroform;
Flow Rate: 1 ml/min;
Amount of Sample: 100 $\mu$l (0.5 W/W % of a sample was dissolved in chloroform);
Column Temperature: 40° C.

Preperation Examples 1–8

Preparations of Poly-L-lactide

PLLA polymers (Lot Nos. 1–8) were synthesized by conventional bulk ring opening polymerization of L-lactide. Each of the obtained PLLA materials (granular) had weight-average molecular weight of 200,000–220,000. The granular PLLAs were subjected to vacuum thermodrying (under a reduced pressure of 1–10 mmHg, at 120° C., for 10 hours) to give granular PLLA polymers that were reduced in lactide contents.

Each of the granular PLLA polymers was directly molded by an extruder without being pelletized, at a molding temperature of 200–210° C. to give a PLLA bullet in the form of a cylinder having a diameter of $\phi$16 mm. The PLLA bullets were subjected to vacuum thermodrying (under a reduced pressure of 1–10 mmHg, at 120° C., for 10 hours) to give PLLA bullets that were reduced in lactide contents. Further, each of the PLLA bullets was drawn at a draw ratio of 2.5 by using a hydrostatic extruder at a mold temperature of 120–140° C. to prepare a PLLA rod of $\phi$10 mm. Each of the PLLA drawn rods was cut to prepare a PLLA screw sample having a crest diameter of $\phi$ 4.5 mm and a overall length of 30 mm (samples No. 1–No. 8). Weight-average molecular weights measured by GPC and residual lactide contents of the samples measured by HPLC are shown in Table 1.

Text Example 1

Measurements of Retention of Pull-out Strength

After immersing the screw samples Nos. 1–8 obtained by Preparation Examples 1–8 in PBS (pH 7.4) at 37° C. for 3 months, retention of pull-out strength of each of the samples was measured.

A pull-out test was carried out by using AUTOGRAPH AG-5000B, a product of Shimadzu Corporation, at a test speed of 1 mm/min. By way of a degradability test, measured were physical properties of the samples which had been immersed in a phosphate buffered saline (PBS) and taken out after a predetermined period of time. Results are shown in Table 1 and FIG. 1.

TABLE 1

| Sample | Molecular Weight | Residual Lactide (ppm) | Retention of Pull-out Strength (%) |
|---|---|---|---|
| No. 1 | 189,000 | 1319 | 93 |
| No. 2 | 176,000 | 1442 | 90 |
| No. 3 | 149,000 | 1874 | 89 |
| No. 4 | 187,000 | 3298 | 87 |
| No. 5 | 181,000 | 3959 | 82 |
| No. 6 | 179,000 | 4236 | 70 |
| No. 7 | 174,000 | 4569 | 45 |
| No. 8 | 169,000 | 4638 | 26 |

From the results shown in Table 1 and FIG. 1, it was confirmed that the retention of pull-out strength changes sharply at around 4,000 ppm of the residual lactide.

Test Example 2

Measurement of Retention of Flexural Strength

Granular PLLA polymers each having a lactide content of 100 ppm, 2,500 ppm and 5,000 ppm were synthesized by conventional bulk ring opening polymerization of L-lactide. Obtained granular PLLA polymers were subjected to vacuum thermodrying (at a reduced pressure of 1–10 mmHg, at 120° C., for 10 hours) to give granular PLLA polymers reduced in lactide contents.

Each of the granular PLLA polymers was directly molded by an extruder without being pelletized at a molding temperature of 200–210° C. to give a PLLA bullet in the form of a cylinder having a diameter of φ16 mm. The PLLA bullets were subjected to vacuum thermodrying (under a reduced pressure of 1–10 mmHg, at 120° C., for 10 hours) to give PLLA bullets reduced in lactide contents. Further, each of the PLLA bullets was drawn at a draw ratio of 2.5 by using a hydrostatic extruder at a molding temperature of 120–140° C. to prepare a PLLA rod of φ10 mm. The PLLA drawn rods were cut to give pins (φ 3.5 mm) as samples (each having a lactide content of 80 ppm (weight-average molecular weight measured by GPC of 130,000), 1,400 ppm (weight-average molecular weight measured by GPC of 156,000) and 4,800 ppm (weight-average molecular weight measured by GPC of 131,000). Retention of flexural strength of each of the samples was measured after being immersed in PBS (pH 7.4) at 37° C. for 10 months.

In addition, the flexural strength was measured in accordance with JISK7203. The retention of flexural strength (%) was calculated from an expression of (flexural strength after being immersed in PBS for a predetermined period of time)/(initial flexural strength)×100.

Figure 2:
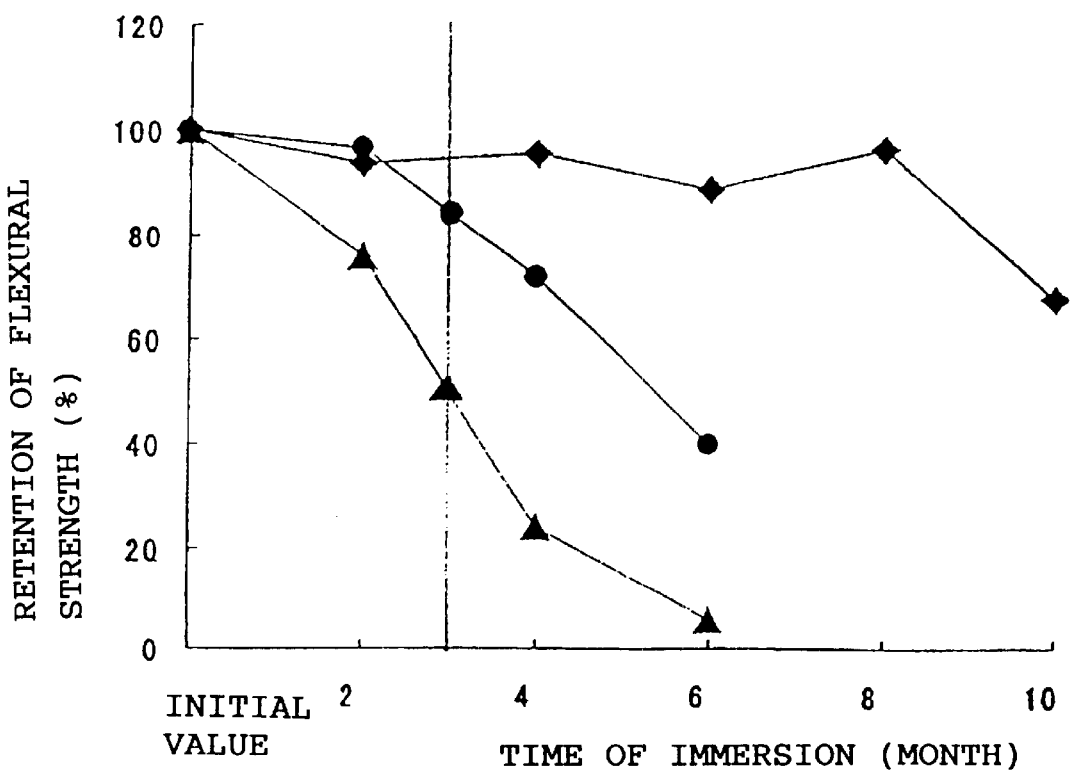
FIG. 2 shows measurement results of retention of flexural strength.

Results are shown in FIG. 2. The symbols in FIG. 2 denote as follows: ♦ (lactide content of 80 ppm), ● (lactide content of 1,400 ppm) and ▲ (lactide content of 4,800 ppm). Retention of flexural strength after 3 months of immersion of the sample containing 4,800 ppm of lactide is 50%, that of the sample containing 1,400 ppm of lactide is 85%, and that of the sample containing 80 ppm of lactide is 95%.

Test Example 3

As to Retention of Pull-out Strength

Figure 3:
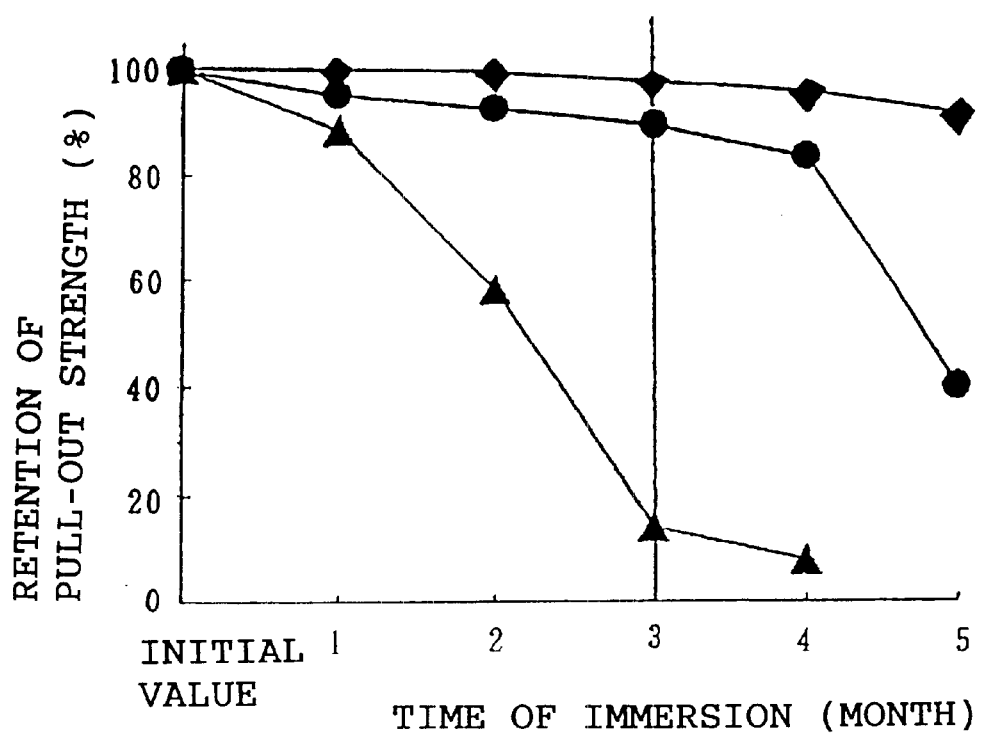
FIG. 3 shows measurement results of retention of pull-out strength.

The screw samples each containing 80 ppm, 1,400 ppm and 4,800 ppm of lactide, which were obtained by cutting PLLA drawn rods used in Test Example 2, were measured for retention of pull-out strength in the same manner as in Test Example 1. Results are shown in FIG. 3. The symbols in FIG. 3 denote as follows: ♦ (lactide content of 80 ppm), ● (lactide content of 1,400 ppm) and ▲ (lactide content of 4,800 ppm). Retention of flexural strength after 3 months of immersion of the sample containing 80 ppm of lactide is 98%, that of the sample containing 1,400 ppm of lactide is 90%, and that of the sample containing 4,800 ppm of lactide is 15%.

Test Example 4

Washing with Acetone

Granular PLLA polymer having weight-average molecular weight of 1273,400 (measured by GPC) was subjected to vacuum thermodrying (under a reduced pressure of 1–10 mmHg, at 120° C., for 10 hours) to give granular PLLA polymer reduced in a lactide content. The granular PLLA polymer was pelletized, and a part the PLLA pellets was washed with acetone for 10 hours using a Soxhlet extractor. The washed PLLA pellets were placed in a vacuum thermodryer to remove acetone under the conditions at 120° C., for 10 hours under 1–10 mmHg.

Each of the acetone-washed PLLA pellets and acetone-unwashed PLLA pellets were subjected to bullet molding by using am injection molding machine, drawing using a hydrostatic extruder (at a draw ratio of 2.5) and a cutting process in the same manner as in Preparation Examples 1–8, thereby preparing PLLA screw samples each having a crest diameter of φ 4.5 mm and an overall length of 30 mm. The PLLA screw sample which was not washed with acetone had a lactide content of 4,200 ppm and weight-average molecular weight of 250,000.

In turn, the screw sample which was washed with acetone had a lactide content of 1,000 ppm and weight-average molecular weight of 310,000.

Figure 4:
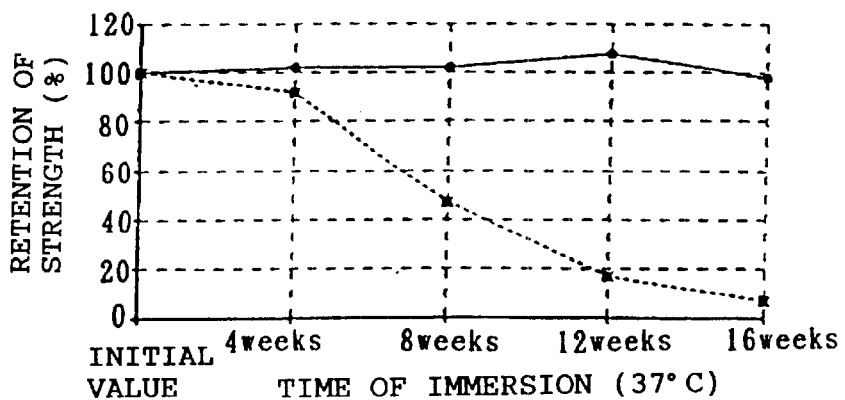
FIG. 4 shows results obtained by testing the acetone-washed PLLA sample.
Figure 4:
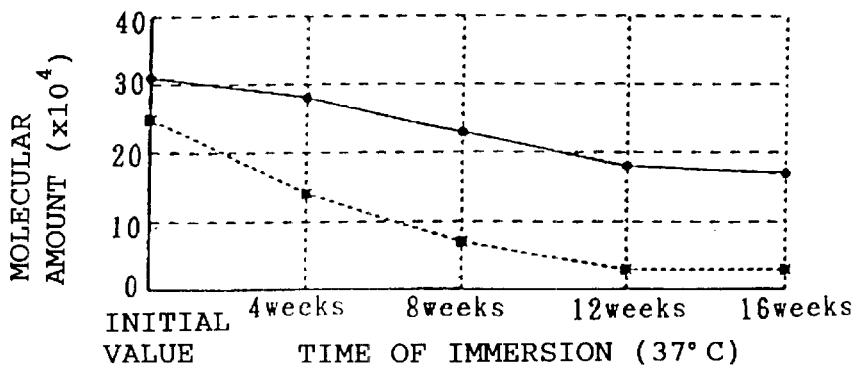
Figure 4:
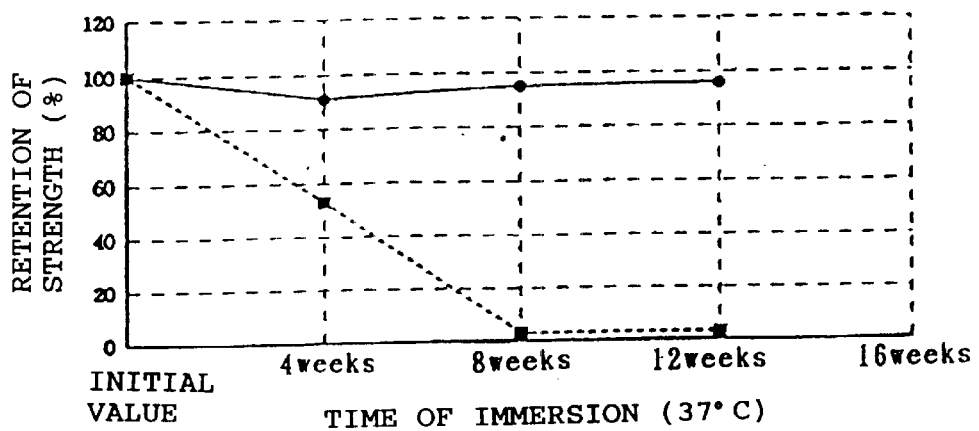

Results are shown in Table 2, Table 3 and FIG. 4. In FIG. 4, ● denotes the acetone-washed PLLA sample and ■ denotes the acetone-unwashed PLLA sample.

TABLE 2

Molecular Weight, Retention of Flexural Strength and Retention of Pull-Out Strength of Acetone-Washed PLLA Sample

| Time of Immersion | Molecular Weight | Retention of Flexural Strength (%) | Retention of Pull-out Strength |
|---|---|---|---|
| Initial Value | 310,000 | 100 | 100 |
| 4 weeks | 280,000 | 102 | 91 |
| 8 weeks | 230,000 | 102 | 95 |

TABLE 2-continued

Molecular Weight, Retention of Flexural Strength and
Retention of Pull-Out Strength of Acetone-Washed PLLA
Sample

| Time of Immersion | Molecular Weight | Retention of Flexural Strength (%) | Retention of Pull-out Strength |
|---|---|---|---|
| 12 weeks | 180,000 | 108 | 96 |
| 16 weeks | 170,000 | 98 | — |

TABLE 3

Molecular Weight, Retention of Flexural Strength and
Retention of Pull-Out Strength of Acetone-Unwashed PLLA
Sample

| Time of Immersion | Molecular Weight | Retention of Flexural Strength (%) | Retention of Pull-out Strength |
|---|---|---|---|
| Initial Value | 250,000 | 100 | 100 |
| 4 weeks | 140,000 | 92 | 53 |
| 8 weeks | 70,000 | 47 | 3 |
| 12 weeks | 30,000 | 17 | 3 |
| 16 weeks | 30,000 | 7 | — |

What is claimed is:

1. A medical material comprising a lactide-containing polymer having weight-average molecular weight measured by GPC of less than 400,000, and having a lactide content of not more than 4,000 ppm, wherein the medical material is produced by a process comprising reducing a lactide content to not more than 4,000 ppm by treating the lactide-containing polymer by a pressure-reducing step during polymerization.

2. The medical material according to claim 1, wherein initial flexural strength is not less than 100 MPa and flexural strength after being immersed in a phosphate buffered saline (PBS) at 37° C. for 90 days is not less than 80% of the initial strength.

3. The medical material according to claim 1, wherein the medical material is a bone fixation device.

4. The medical material according to claim 3, wherein the bone fixation device is a pin, a screw, a nail, an intramedullary nail, a plate, a washer, a staple, an anchor or a wire.

5. A process for producing a medical material comprising reducing a lactide content to not more than 4,000 ppm by treating a lactide-containing polymer by a pressure-reducing step during polymerization.

6. A method for adjusting retention of strength of a medical material, wherein the medical material comprises a lactide-containing polymer, the method comprising adjusting a lactide content to not more than 4,000 ppm by treating the lactide-containing polymer by a pressure-reducing step during polymerization.

7. A medical material according to claim 1, wherein the lactide content is not more than 3,500 ppm.

8. A medical material according to claim 1, wherein the lactide content is not more than 3,000 ppm.

9. A medical material according to claim 1, wherein the lactide content is not more than 2,000 ppm.

10. A medical material according to claim 1, wherein the lactide content is not more than 1,000 ppm.

11. A medical material comprising a lactide-containing polymer having weight-average molecular weight measured by GPC of less than 400,000, and having a lactide content of not more than 4,000 ppm, wherein the medical material is produced by a process comprising reducing a lactide content to not more than 4,000 ppm by vacuum thermodrying the lactide-containing polymer at a pressure of about 1–10 mm Hg for about 10–20 hours at a temperature of about 120° C.

12. A medical material comprising a lactide-containing polymer having weight-average molecular weight measured by GPC of less than 400,000, and having a lactide content of not more than 4,000 ppm, wherein the medical material is produced by a process comprising reducing a lactide content to not more than 4,000 ppm by washing the lactide-containing polymer with a solvent, wherein washing with a solvent comprises subjecting the lactide-containing polymer to Soxhlet extraction for 5 to 12 hours.

13. The medical material according to any one claims 7 to 10, wherein the medical material is produced by a process comprising reducing a lactide content by treating the lactide-containing polymer at a pressure of about 1–10 mm Hg for about 10–20 hours at a temperature of about 120° C.

14. The medical material according to claim 1, wherein the lactide-containing polymer has weight average molecular weight measured by GPC of 100,000–250,000.

15. The medical material according to claim 11, wherein the lactide-containing polymer has weight average molecular weight measured by GPC of 100,000–250,000.

16. The medical material according to claim 13, wherein the lactide-containing polymer has weight average molecular weight measured by GPC of 100,000–250,000.

* * * * *